United States Patent [19]

Olsen

[11] Patent Number: 5,800,415

[45] Date of Patent: *Sep. 1, 1998

[54] STABLE ADHESIVE OSTOMY APPLIANCE

[75] Inventor: Hans Olsen, Hørsholm, Denmark

[73] Assignee: Coloplast A/S, Denmark

[*] Notice: This patent issued on a continued prosecution application filed under 37 CFR 1.53(d), and is subject to the twenty year patent term provisions of 35 U.S.C. 154(a)(2).

[21] Appl. No.: 654,663

[22] Filed: May 29, 1996

[30] Foreign Application Priority Data

May 29, 1995 [DK] Denmark .................................. 0607/95

[51] Int. Cl.$^6$ .......................................................... A61F 5/44
[52] U.S. Cl. ......................... 604/336; 604/332; 604/338; 604/341
[58] Field of Search ..................... 604/344, 332, 604/336, 338, 339, 342

[56] References Cited

U.S. PATENT DOCUMENTS 5,496,296  3/1996  Holmberg .............................. 604/344

FOREIGN PATENT DOCUMENTS 2760432A  7/1988  European Pat. Off. ............... 604/344

*Primary Examiner*—Robert A. Clarke
*Attorney, Agent, or Firm*—Ostrolenk, Faber, Gerb & Soffen, LLP

[57] ABSTRACT

An ostomy collecting system has a collecting bag having an inlet opening in a bag wall and surrounding connecting elements for connection with a stoma, and a carrier device for the collecting bag. Which is a base plate and a substantially annular first flange connected to the base plate via a first connecting section. The connecting elements comprise a substantially annular second flange, fixedly connected to the collecting bag via a substantially annular second connecting section. The two flanges are connected with the base plate and the collecting bag, respectively, in such a manner that the outer radius of said second connecting section exceeds the outer radius of said first connecting section by a value which at least equals the total thickness of the two flanges. The collecting bag, carrier device connections is provided by adhesive on said second flange capable of repeated adhesion with the first flange, and the two flanges are made from a flexible and resilient material and can be as discs of cellular plastic material.

8 Claims, 2 Drawing Sheets

STABLE ADHESIVE OSTOMY APPLIANCE

BACKGROUND OF THE INVENTION AND PRIOR ART

The present invention relates to an ostomy collecting system for use by patients having a stoma.

From EP patent application No. 0 276 043 a collecting system of this type is known, comprising, on one hand, a collecting bag having an inlet opening formed in a bag wall and connecting elements surrounding said inlet opening for connection with a stoma in a user, and, on the other hand, a carrier device for the collecting bag, said carrier device comprising a base plate for fastening on the user and a substantially annular first flange fixedly connected to the base plate via a substantially annular first connecting section, said connecting elements comprising a substantially annular second flange fixedly connected to the collecting bag via a substantially annular second connecting section and adapted for removable and adhesive connection with said first flange. In this prior art system, a flange for adhesive connection with the flange of the collecting bag or with the bag itself being fastened on a base plate is in the form of an adhesive pad.

In such a collecting system, the base plate of the carrier device must be able to remain on the user over a long period of time, for example up to 8–10 days. During this whole period of time, the carrier device must be capable of undergoing deformation owing to the user's movements, washing, exposure to bag replacements, etc. Conventionally, the base plate of such a carrier device is designed as a thin adhesive foil, optionally with some sort of stiffening reinforcement disc for maintaining a plane adhesive surface for the bag. However, such a reinforcement disc prevents the base plate from following the contours of the body when the user moves, and it does not provide the desired shock absorbing effect between the collecting bag and the user, which, of course, reduces comfort. A less rigid disc would be able to follow the base plate during such movements, to be sure, but would thus exert a pull in it, which, in addition to transmitting an unpleasant pulling effect to the user's skin, also weakens the adhesive effect between base plate and skin. Furthermore, the adhesive surface facing the bag will not in that case remain plane owing to the inevitable deformations, which results in problems of rearranging the bag on the user.

In the above EP patent application, an attempt has been made to eliminate these problems by connecting a rigid flange with the base plate via a flexible sheet, which, however, provides an unstable and insecure connection. Furthermore, the adhesive connection taught between bag and carrier device is provided either by a number of layers of adhesive applied to the flange of the base plate and activated one after the other, which reduces the number of times to which the base plate may be exposed to a change of bag to the number of layers of adhesive, or by using a new bag with a fresh layer of adhesive, which renders the system more expensive in use.

SUMMARY OF THE INVENTION

Against this background, the object of the present invention is to provide a collecting system of the type mentioned in the introduction, in which the connecting surface between the collecting bag and the carrier device is maintained largely independently of the deformation of the base plate caused by, for example, the user's movements, but which is nevertheless stable and continues to exhibit an even and flexible adhesive surface without creases and ditches between the flanges of the bag and the base plate. It is a further object that it must be possible to remove and reinstall one or more bags repeatedly without any reduction in the life of the base plate.

According to the invention, an ostomy collecting system is provided, comprising, on one hand, a collecting bag having an inlet opening formed in a bag wall and connecting elements surrounding said inlet opening for connection with a stoma in a user, and, on the other hand, a carrier device for the collecting bag, said carrier device comprising a base plate for fastening on the user and a substantially annular first flange fixedly connected to the base plate via a substantially annular first connecting section, said connecting elements comprising a substantially annular second flange fixedly connected to the collecting bag via a substantially annular second connecting section and adapted for removable and adhesive connection with said first flange, said first and second flanges being connected with the base plate and the collecting bag, respectively, in such a manner that the outer radius of said second connecting section exceeds the outer radius of said first connecting section by a value which at least equals the total thickness of the first and the second flanges, the adhesive connection between the collecting bag and the carrier device being provided by a layer of adhesive applied on said second flange and capable of repeated adhesion with said first flange, said first and second flanges being made from a flexible and resilient material.

This design of the collecting system according to the invention achieves a connection between carrier device and collecting bag, which is stable against displacement forces, and which acts as a shock absorbing element. The difference in radius between the two connecting sections between the first flange and the base plate, and the second flange and the collecting bag, respectively, has the result that the force which would normally be transmitted to the user's skin during use of the collecting system will instead be absorbed by the flanges, which in this design are capable of deformation both in the plane of the flanges and at a right angle thereto, as the point of action of the force will be located in a cantilever area, which provides a good resilient effect. The flange connected with the base plate exhibits a good adhesive surface, as the resilience of both the first and the second flanges causes them to return to their original plane state after deformation. Finally, the reusable layer of adhesive on the flange connected with the collecting bag means that the bag can be removed from the carrier device repeatedly, and that, for example, in case of venting, when the bag is merely lifted, it is not necessary to activate a new layer of adhesive or use a new bag.

The first and the second flanges are preferably formed as discs of a cellular plastic material, which provides a good shock absorbing and resilient action and also has the effect that the weight of the collecting system can be kept down.

The layer of adhesive may be washable and the first and second flanges may be disks of a cellular plastic material such as a polyurethane cellular plastic or an ethylene vinyl acetate cellular plastic. Also, the layer of adhesive on the second flange can have a layer thickness substantially smaller than the thickness of the second flange.

BRIEF DESCRIPTION OF THE DRAWINGS

The invention will now be described in further detail below with reference to the schematic drawing, in which.

DETAILED DESCRIPTION OF THE PREFERRED EMBODIMENTS

Figure 2:
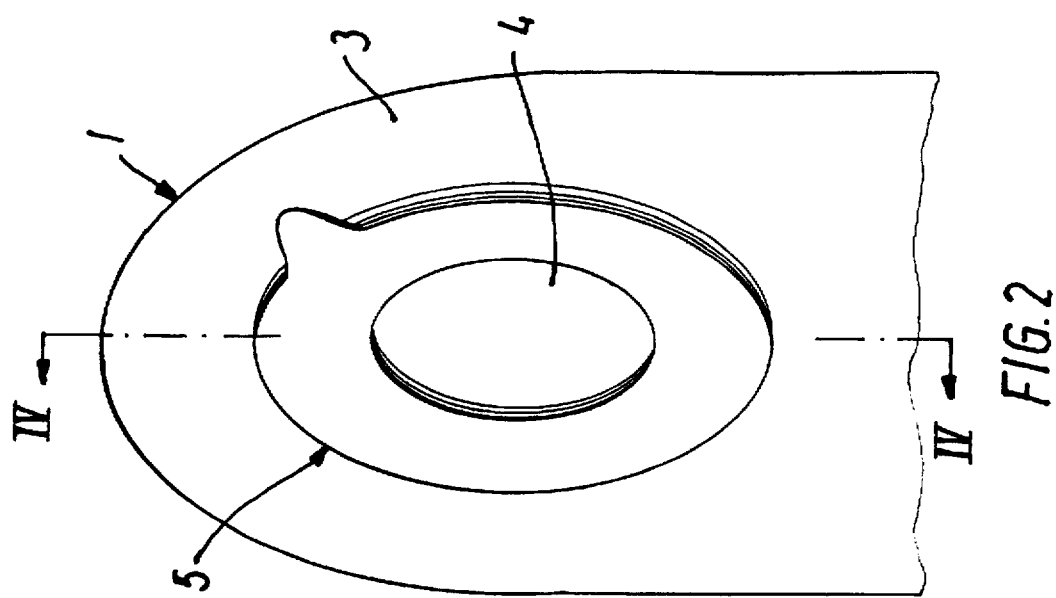
FIGS. 1 and 2 show perspective views of a carrier device and a collecting bag, respectively, of a collecting system according to the invention.
Figure 1:
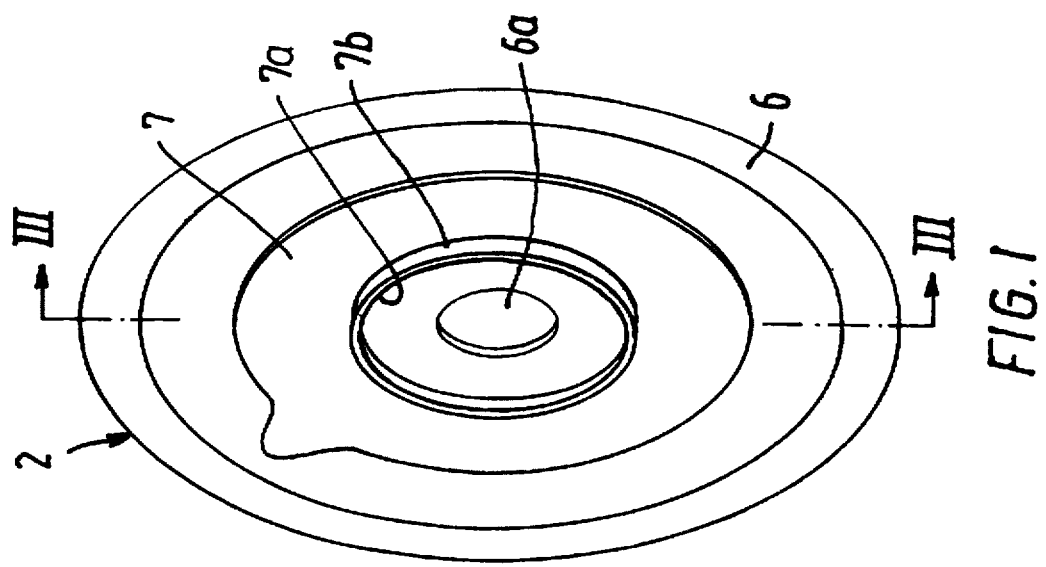

The ostomy collecting system shown in FIGS. 1 and 2 comprises a collecting bag 1 for collection of faeces and a carrier device 2 for fastening the bag 1 around an intestinal orifice in the form of a so-called stoma in the user's abdominal wall, and for this purpose has an inlet opening 4 in a bag wall 3. The bag 1 may either be closed at the bottom as shown (FIG. 4) or be formed with a drainage device for emptying of its contents. The inlet opening 4 is surrounded by connecting elements generally designated 5 for connecting the bag 1 with the carrier device 2. The carrier device comprises a base plate 6 with a hole 6a which is designed to be adhered to the user's skin by means of a skin-friendlly adhesive applied on the back of the base plate. The base plate 6 carries a first flange or base plate flange 7, in which is formed a hole 7a with an upright collar 7b, the function of which will be explained below.

Figure 3:
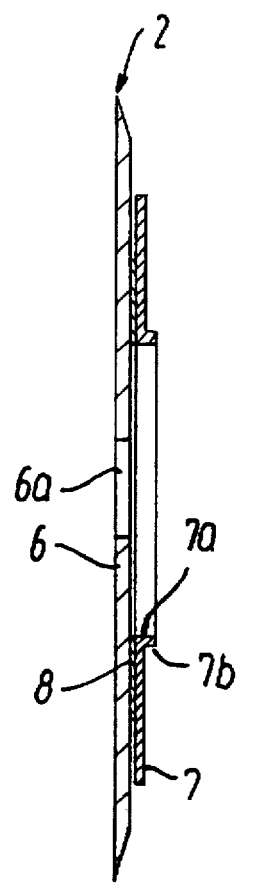
FIG. 3 shows a section along the line III—III in FIG. 1.
Figure 4:
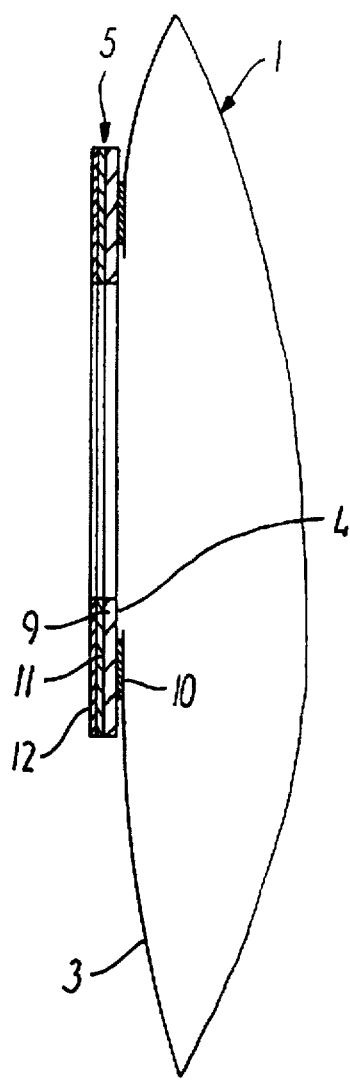
FIG. 4 shows a section along the line IV—IV in FIG. 2.

The structure of the carrier device 2 and the collecting bag 1 with associated connecting elements 5 is shown in further detail in FIGS. 3 and 4, respectively.

As it appears, the base plate flange 7 is fastened to the base plate 6 with a layer 8 of adhesive applied in a substantially annular connecting section having an internal diameter corresponding to that of the hole 7a in the base plate flange 7 and having an external diameter so that a rim portion of the flange 7 protrudes beyond the layer 8 of adhesive. The base plate flange 7 may, for example, be moulded in a water-repellent cellular plastic material, such as ethylene vinyl acetate (EVA) or polyurethane (PUR), with closed cells so that the cellular plastic material does not absorb liquid.

The fastening elements 5 on the bag 1 are constructed from a second flange or bag flange 9 which, in the embodiment shown, is fastened to the bag wall 3 by means of a substantially annular connecting section in the form of a layer 10 of adhesive in such a manner that a rim portion of the bag flange 9 protrudes beyond the layer 10 of adhesive. The outer radius of the layer 10 of adhesive exceeds the outer radius of the layer 8 of adhesive between the base plate flange 7 and the base plate 6 by a value at least equalling the total thickness of the base plate flange 7 and the bag flange 9. Of course, the bag flange 9 may also be fastened to the bag 3 through other means, or example by welding, and like the base plate flange 7 it consists of a moulded cellular plastic material, such as EVA cellular plastic or PUR cellular plastic. On the side facing away from the bag, over substantially all its surface the flange 9 is coated with a thin, washable layer 11 of adhesive, which may, for example, be a hydrogel adhesive, an acrylate adhesive or an adhesive of the hot-melt type. The layer 11 of adhesive is applied in a thin layer, partly to keep down thickness, partly to maintain the flexibility and resilience of the bag flange. This application may be effected, for example, by coating, spraying or application in a suitable pattern. In the delivery state of the bag, the layer 11 of adhesive is covered by an adhesive-repellent cover layer 12.

When the collecting system according to the invention is used, the carrier device 2 is arranged on the user, the base plate 6 being placed against the user's skin, and the stoma being passed out through the hole 6a. The cover layer 12 of the collecting bag is removed to uncover the layer 11 of adhesive, which is subsequently adhered to the base plate flange 7 of the carrier device with simultaneous insertion of the stoma into the collecting bag through the inlet opening 4. At this stage, the upright collar 7b acts as a guide surface and thus prevents incorrect mounting of the collecting bag, and in the assembled state of the collecting system it forms a passage for the stoma and thus protects the layer 11 of adhesive from faeces flowing out from the intestine.

I claim:

1. An ostomy collecting system comprising a collecting bag having an inlet opening formed in a bag wall and connecting elements surrounding said inlet opening for connection with a stoma in a user, and a carrier device for the collecting bag, said carrier device comprising a base plate for fastening on the user and a substantially annular first flange firmly connected with the base plate via a substantially annular first connecting section, said connecting elements comprising a substantially annular second flange firmly connected with the collecting bag via a substantially annular second connecting section and adapted for removable and adhesive connection with said first flange, said first and second flanges being connected with the base plate and the collecting bag, respectively, such that the outer radius of said second connecting section exceeds the outer radius of said first connecting section by a value which at least equals the total thickness of the first and the second flanges, the adhesive connection between the collecting bag and the carrier device being provided by a layer of adhesive on said second flange capable of repeated adhesion with said first flange, said first and second flanges being both made from a flexible and resilient material capable of deformation both in the plane of the flanges and at right angles thereto, thereby providing a cantilever area to secure adsorption of load forces from the bag by the resilient first and second flanges.

2. The ostomy collecting system according to claim 1, wherein the layer of adhesive is washable.

3. The ostomy collecting system according to claim 1, wherein said first and second flanges are discs of a cellular plastic material.

4. The ostomy collecting system according to claim 3, wherein said cellular plastic material is a polyurethane cellular plastic.

5. The ostomy collecting system according to claim 3, wherein said cellular plastic material is an ethylene vinyl acetate cellular plastic.

6. The ostomy collecting, system according to claim 3, wherein the layer of adhesive is washable.

7. The ostomy collecting system according to claim 6, wherein said layer of adhesive on the second flange has a layer thickness substantially smaller than the thickness of said second flange.

8. The ostomy collecting system according to claim 1, wherein said layer of adhesive on the second flange has a layer thickness substantially smaller than the thickness of said second flange.

* * * * *